US00PP10294P

United States Patent [19]

Glaser

[11] Patent Number: Plant 10,294

[45] Date of Patent: Mar. 24, 1998

[54] AZALEA PLANT NAMED MELODIE

[76] Inventor: Karl Glaser, Alte Strasse 9, D-64832 Babenhausen, Germany

[21] Appl. No.: 651,722

[22] Filed: May 22, 1996

[51] Int. Cl.[6] ..... A01H 5/00

[52] U.S. Cl. ..... Plt./56

[58] Field of Search ..... Plt./56

[56] References Cited

U.S. PATENT DOCUMENTS

P.P. 1,158 12/1952 Brooks ..... Plt./56

OTHER PUBLICATIONS

UPOV-ROM, 1997-03. Citation for Azalea named 'Melodie' DE PBR RDG 00107. Denomination proposed Jun. 24, 1992, accepted Jan. 26, 1993.

*Primary Examiner*—James R. Feyrer
*Assistant Examiner*—Melissa L. Kimball
*Attorney, Agent, or Firm*—Foley & Lardner

[57] ABSTRACT

An azalea plant named Melodie particularly characterized by its evergreen foliage, double flower form, light salmon-pink flower color with red flecks and white margin, free branching, compact semi-upright plant habit, uniform flowering response in a year round controlled program, and by its good cooler tolerance and keeping quality.

1 Drawing Sheet

The present invention comprises a new and distinct cultivar of Azalea, a greenhouse forcing type, hereinafter referred to as Melodie.

Melodie, identified as US Bunt during the selection process, was discovered as a naturally occurring mutation from the cultivar Komet in Babenhausen, Germany by the inventor Karl Glaser. Melodie was discovered and selected as one flowering plant within a block of flowering plants of the parent cultivar. The parent cultivar is disclosed in a pending application of applicant.

The first asexual reproduction of Melodie was accomplished when vegetative cuttings were taken from the initial selection in April 1987, in Babenhausen, Germany, by technicians working under formulations established and supervised by Karl Glaser.

Horticultural examination of controlled flowerings of successive generations of plants derived from cuttings taken from the original selection has shown that the unique combination of characteristics as herein disclosed for Melodie are fixed and retained through successive generations of asexual reproduction.

Melodie has not been observed under all possible environmental conditions. The phenotype may vary significantly with variations in environment such as temperature, light intensity and day length, without, however, any variance in the genotype.

The following observations, measurements and comparisons describe plants that were grown in Salinas, Calif. in a controlled greenhouse environment and following a commercial schedule.

The following traits have been repeatedly observed and are determined to be basic characteristics of Melodie, which in combination distinguish this azalea as a new and distinct cultivar:

1. A light salmon-pink flower color (43D) with red flecks and white margins upon opening, fading to a lighter pink color (50D) as flowers age.

2. Double flowers, with the flowers ranging from 7.0 to 10.0 cm in diameter, with a 8.5 cm the average size.

3. Compact, semi-upright, free branching plant habit.

4. Uniform response in year round controlled flowering programs, forcing in 36 days on average.

5. Long lasting flowers, with flowers in a simulated home environment lasting up to two weeks.

6. Medium green pubescent evergreen foliage, leathery in appearance.

7. Good foliage retention and no flower bud damage when cooled for 6 weeks with no lighting at 38° F.

The accompanying color photograph shows in perspective view the unique features of the new cultivar, with colors being as true as possible with color illustrations of this type.

Of the commerical cultivars known to the inventor, the most similar in comparison to Melodie is the unpatented cultivar Gloria. Flower color and flower response are very much alike. Melodie differs from Gloria in that Melodie has larger flowers and is more heavily petaled than Gloria. Melodie has green sepals whereas Gloria is hose in hose. Also, the foliage of Melodie is broader and more pubescent than Gloria's.

In the following description color references are made to The Royal Horticultural Society Color Chart. The color values were determined on Apr. 20, 1995. All readings were taken in an office under cool white fluorescent lights, facing a west window between the hours of 10:00 a.m. and 2:00 p.m.

Classification:

*Botanical.*—*Rhododendron hybrida*, evergreen type, c.v. 'Melodie'.

*Commercial.*—Florist forcing pot azalea.

Inflorescence

A. Flowers (general):

*Size.*—7.0 to 10.0 cm.

*Borne.*—Terminal cluster, usually 3 per bud, ranging from 2–3.

*Form.*—Double funnel-form.

*Blooming habit.*—Once, profusely. Buds easily and uniformly in a year round program. The majority of terminal buds break color within one week of the first. Flowering begins approximately 36 days after the start of forcing.

*Fragrance.*—None.

B. Corolla (petals):

*Texture.*—Soft.

*Substance.*—heavy.

*Shape.*—Rounded.

*Color (fully open).*—Approximately 43D light salmon pink with red flecks and white margins, fading to a lighter pink (50D) as flowers age. Upper surface: Edge: White. Center: Variable, mixtures of 43D, 48C to 49A, sectors 42B. Base: 48D. Lower surface: 48D, to 40C under blotch. Blotch: Between 63A to 64A.

C. Bud:
*Size.*—Medium.
*Shape.*—Conoidal.
*Color.*—48D, white edge, sectors of 42D.
*Bud sheath.*—Immature: Light green with light brown hairs. Mature: Brown with light brown hairs.

D. Calyx:
*Form.*—Rounded.
*Color.*—144A.

E. Peduncle:
*Length.*—0.5 to 1.5 cm.
*Strength.*—Strong.
*Aspect.*—Pubescent.

F. Reproductive organs:
*Androecium (stamens).*—Number: 0 to 5; many are fully or partially petaloid. Anthers: Reddish Pink. Filaments: Length: 0.0 to 2.0 cm. Color: Pink. Gynoecium (pistils): Stigma: 54B. Style: Length: 1.5 to 3.5 cm. Color: 52A to 54A. Ovary: Pubescent.

Plant Characteristics

A. Foliage:
*Type.*—Evergreen.
*Arrangement.*—Alternate.
*Shape.*—Elliptic.
*Size.*—Length: 2.0 to 7.0 cm. Width: 1.0 to 3.5 cm.
*Margin.*—Entire.
*Color.*—Immature: Upper surface: Between 144A and 146A. Lower surface: 146D. Mature: Upper surface: 147A. Lower surface: 146B. Texture: Leathery. Tomentum: Present on upper surface. Insignificant.

B. Stems:
*Color.*—Immature: 143B. Mature: Mixture of 164A and 165B. Tomentum: Present, but insignificant.

C. Plant habit: Compact, semi-upright bush which achieves a uniform, symmetrical plant in a six inch pot when pinched three times. Total crop time to the dormant budded stage is 40–42 weeks to produce a plant 30–38 cm in diameter and 30–36 cm in total height. Internode lengths vary widely from 2–20 mm on the same stem.

D. Branching habit: Free branching, producing 2–4 breaks when a vegetative cutting is pinched.

E. Rooting: Roots easily in 8 to 10 weeks with 75° F. soil temperature.

F. Budding ease: Plants produce flower buds easily and uniformly year round with the use of commercially available plant growth regulators. Melodie has a medium natural season response time.

G. Cooler tolerance: Plants placed in a cooler as a means of breaking dormancy perform well. Melodie is tolerant of six weeks in an unlighted cooler at 38° F. without foliage loss or bud damage.

H. Blooming: Plants reach the stage of 12 buds showing color in 36 days on average after the cooler treatment. This varies from 21 to 46 days depending upon temperature and stage of flower bud development at the start of forcing. Melodie flowers uniformly across the plants.

I. Shelf life: When plants are moved to an office or home environment at the stage of eight open flowers, they maintain an attractive appearance for up to two weeks. Flowers are somewhat persistent, only occasionally dropping as flowers become old.

I claim:

1. A new and distinct cultivar of azalea plant named Melodie, as described and illustrated.

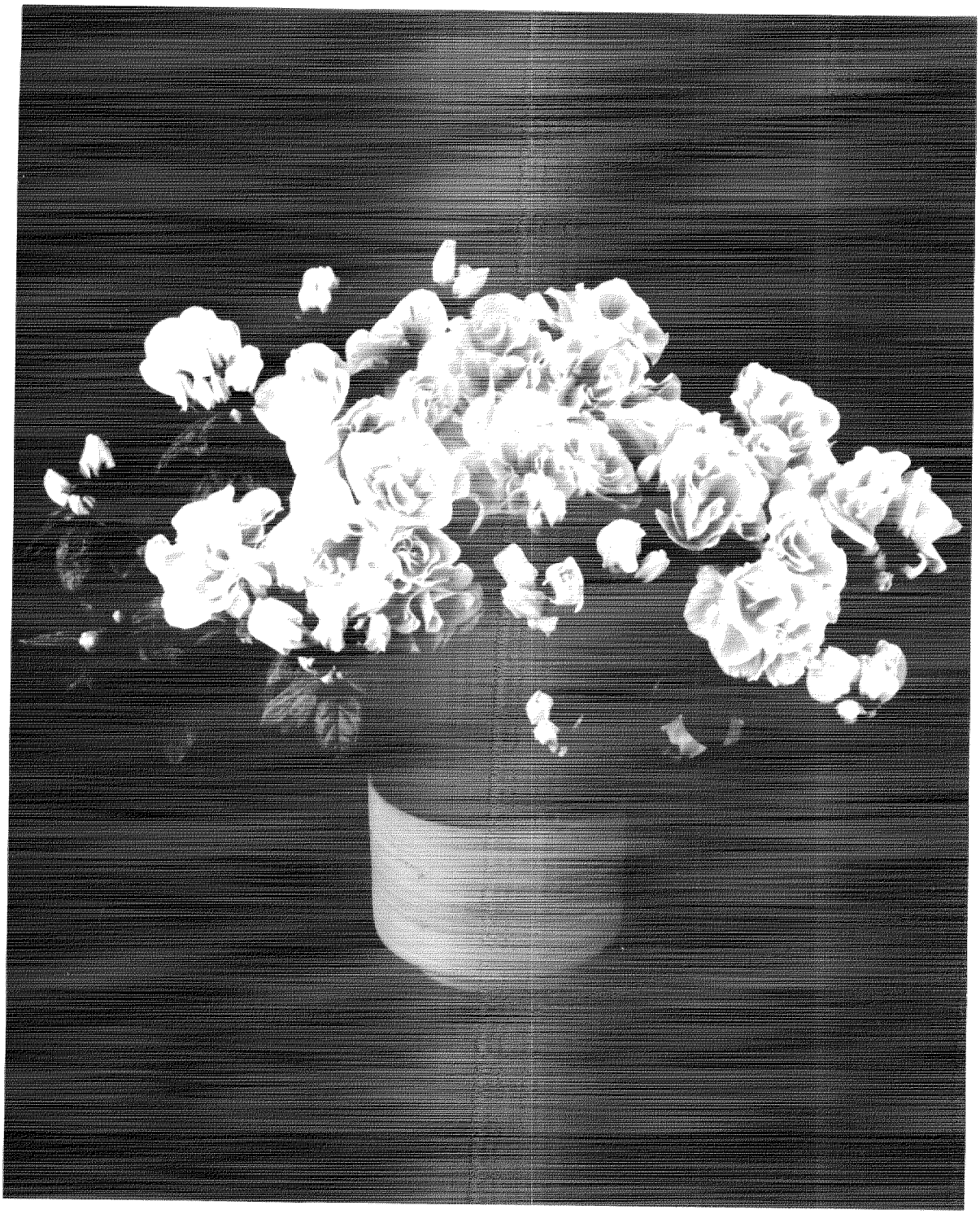

* * * * *